(12) United States Patent
Kammerhofer et al.

(10) Patent No.: US 7,767,869 B2
(45) Date of Patent: Aug. 3, 2010

(54) APPARATUS AND PROCESS FOR THE PRODUCTION OF VINYL CHLORIDE BY THERMAL CRACKING OF 1,2-DICHLOROETHANE

(75) Inventors: Peter Kammerhofer, Burgkirchen (DE); Ingolf Mielke, Burgkirchen (DE); Peter Schwarzmaier, Kastl (DE)

(73) Assignee: Vinnolit Technologie GmbH & Co. KG, Burgkirchen (DE)

( * ) Notice: Subject to any disclaimer, the term of this patent is extended or adjusted under 35 U.S.C. 154(b) by 165 days.

(21) Appl. No.: 10/552,640

(22) PCT Filed: Mar. 17, 2004

(86) PCT No.: PCT/EP2004/002763

§ 371 (c)(1),
(2), (4) Date: Oct. 7, 2005

(87) PCT Pub. No.: WO2004/089860

PCT Pub. Date: Oct. 21, 2004

(65) Prior Publication Data

US 2006/0199983 A1     Sep. 7, 2006

(30) Foreign Application Priority Data

Apr. 11, 2003   (DE) ................. 103 16 987
Jun. 6, 2003    (DE) ................. 103 26 248

(51) Int. Cl.
    *C07C 17/25* (2006.01)
(52) U.S. Cl. .................................................. 570/226
(58) Field of Classification Search ................. 570/226
    See application file for complete search history.

(56) References Cited

U.S. PATENT DOCUMENTS

| 4,788,357 A | 11/1988 | Haselwarter et al. |
| 4,798,914 A * | 1/1989 | Link et al. ............ 570/226 |
| 4,822,932 A * | 4/1989 | Dummer et al. ........ 570/226 |

FOREIGN PATENT DOCUMENTS

EP          0 270 007 A     6/1988

* cited by examiner

*Primary Examiner*—Daniel M Sullivan
*Assistant Examiner*—Sudhakar Katakam
(74) *Attorney, Agent, or Firm*—Edwards Angell Palmer & Dodge LLP; Peter F. Corless; Nicholas J. DiCeglie, Jr.

(57) ABSTRACT

The invention relates to a process for the production of vinyl chloride by thermal cracking, in which the energy balance, the operating time of the cracking furnace and/or the yield of the reaction are distinctly enhanced in comparison with the prior art. A pressure of from 1.4 to 2.5 MPa is established in the cracking coil at a temperature of from 450 to 550° C. and, for pre-heating the EDC (=1,2-dichloroethane) introduced, inter alia the waste heat of the gas stream leaving the top of the quench column is utilized.

10 Claims, 2 Drawing Sheets

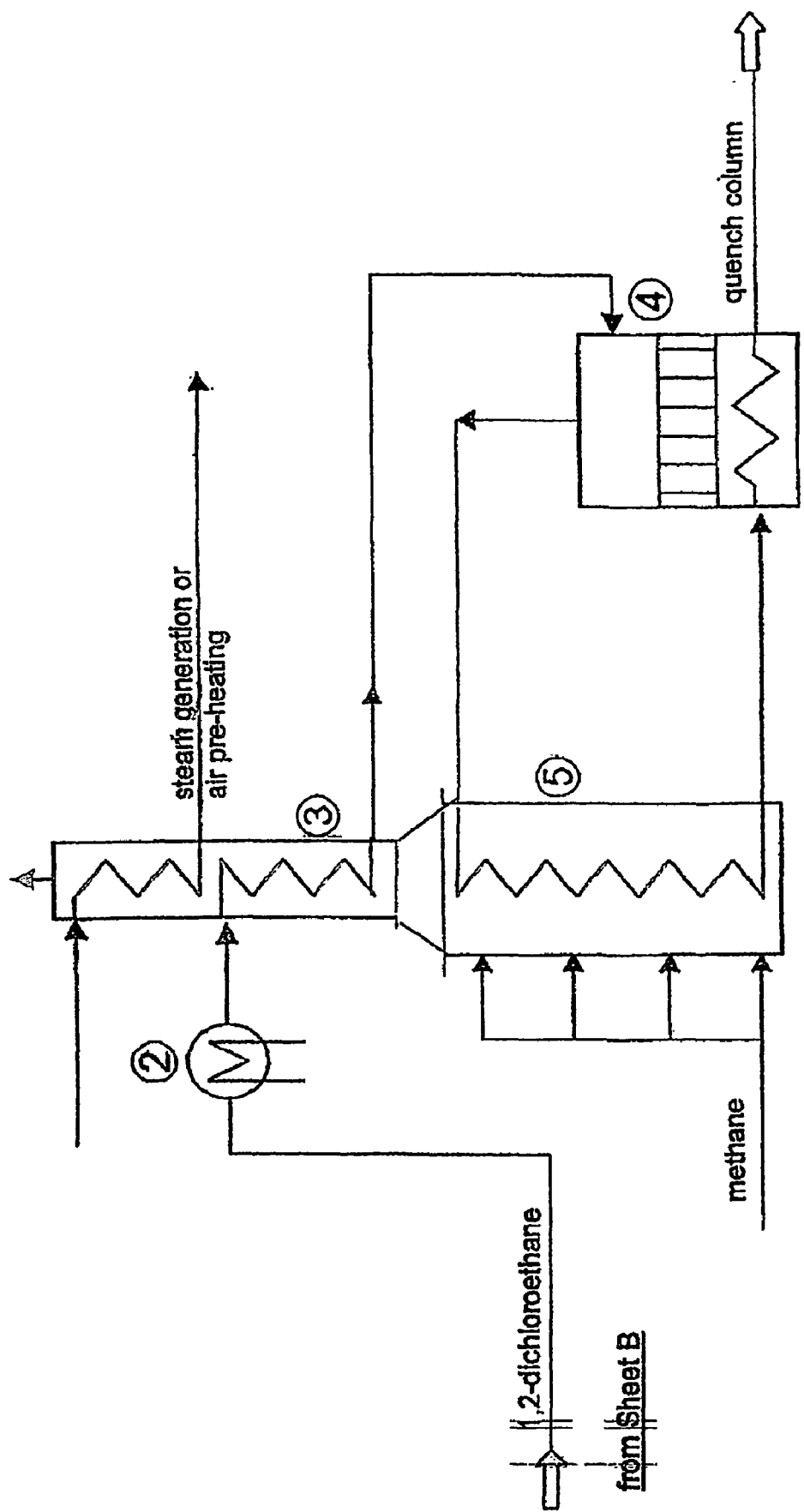
Figure 1, Sheet A

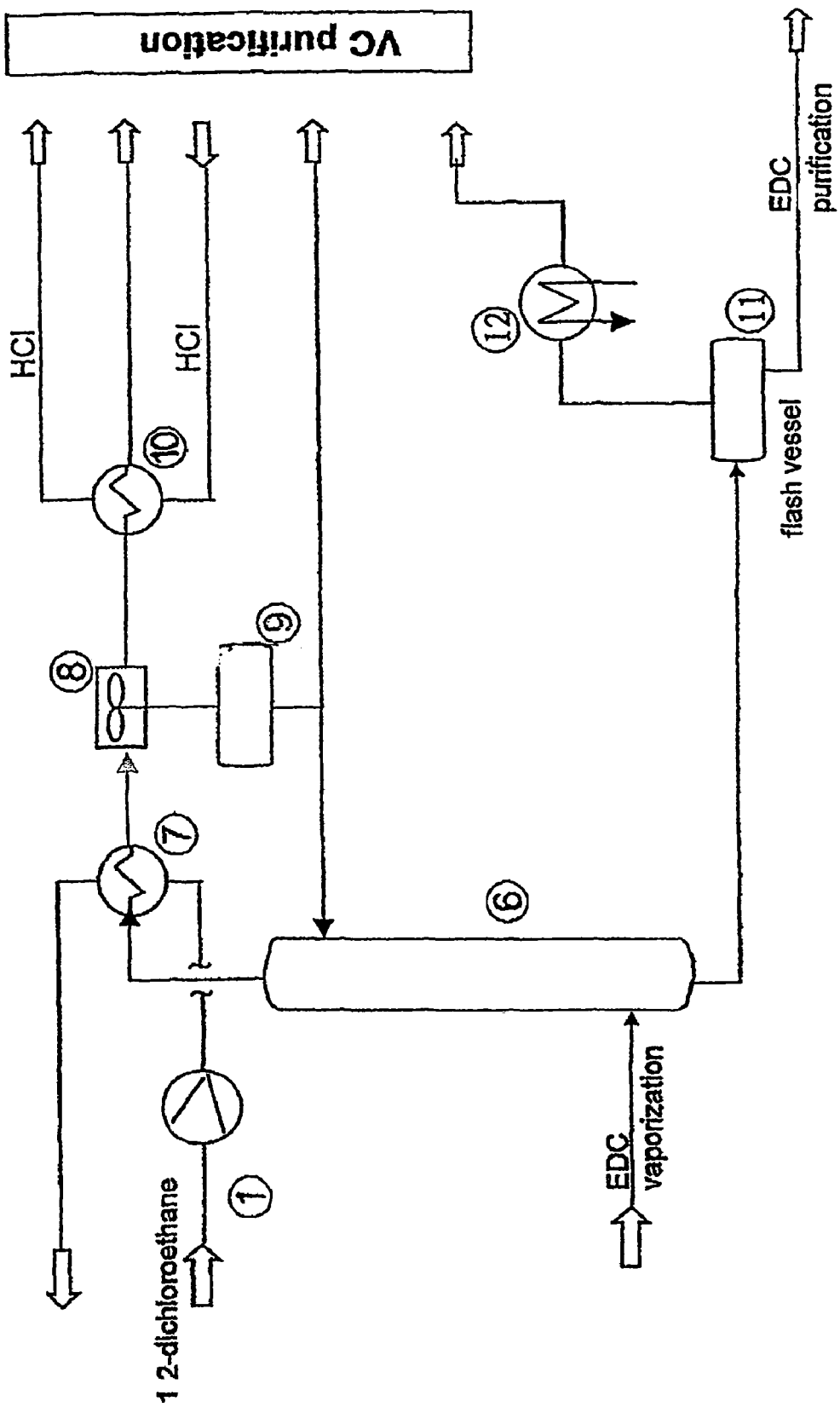
Figure 1, Sheet B

APPARATUS AND PROCESS FOR THE PRODUCTION OF VINYL CHLORIDE BY THERMAL CRACKING OF 1,2-DICHLOROETHANE

The invention relates to a process for the production of vinyl chloride by thermal cracking of 1,2-dichloroethane (EDC) in which it has been possible to improve the energy balance, the operating time (maintenance interval) of the cracking furnace and/or the yield of vinyl chloride in comparison with the prior art (cf. Table 1).

Processes for the production of vinyl chloride by thermal cracking are known, for example, from DE 34 40 685. The latter describes heating the 1,2-dichloroethane in the convection zone of the cracking furnace, vaporizing it with steam in an external heat exchanger (EDC vaporizer) and feeding it in gaseous form into the cracking furnace at a temperature of 195° C. under a pressure of 1.3 MPa (low-pressure process). The cracking gases are subsequently fed for working-up. In the entire system, there is a low system pressure of 1.3 MPa, which has a detrimental effect; when removing hydrogen chloride a high condensation energy is required since the condensation of the gas has to be carried out at very low temperature. In addition, the high thermal energy with which the cracking gas stream leaves the cracking furnace (494° C.) is not put to use.

Disadvantages of that process are especially
a) the high power consumption per tonne of target product for generating the refrigeration energy necessary for condensation and hence removal of the by-product hydrogen chloride
b) the high expenditure of energy which the vaporization of the EDC requires before it is fed into the cracking furnace and
c) the greater energy requirement in the cracking furnace resulting from the low entry temperature of the EDC into the cracking furnace of approximately only 195° C.

There is also known from EP 0 264 065 B1 a process for the production of vinyl chloride by thermal cracking wherein the thermal energy of the cracking gas (that is to say, the gas stream that leaves the radiation zone of the cracking furnace and the temperature of which at that point is said to be about 496° C.) is partly utilized by a heat exchanger in which EDC that has already been passed through the convection zone of the cracking furnace and has thus been heated is vaporized. In that case also, however, the thermal energy of the vapour leaving the quench column which follows the cracking furnace is not put to use. In addition, the pressure in the cracking furnace is relatively high (greater than 2.5 MPa, high-pressure cracking), so that slight temperature fluctuations lead to extreme pressure fluctuations. For example, pressure fluctuations in the EDC vaporizer upstream of the cracking furnace, which affect the reaction time and hence the residence time of the dichloroethane in the cracking furnace, cannot be compensated for.

The object of the invention is therefore to provide an apparatus and a process for the production of vinyl chloride by thermal cracking of 1,2-dichloroethane (EDC), in which the economic efficiency is improved in comparison with the prior art.

The invention relates to an apparatus for the production of vinyl chloride by thermal cracking of 1,2-dichloroethane, comprising at least a cracking furnace, a quench column and a purification facility in that order, wherein, in the feed line through which 1,2-dichloroethane is fed into the radiation zone of the cracking furnace, a predetermined pressure in the range of from 1.4 to 3.5 or 1.5 to 3.5 or 1.4 to 2.5 MPa is ensured and at least a first heat exchanger is arranged by means of which pressure fluctuations and temperature fluctuations in the EDC vaporization are compensated for.

The invention also relates to a process for the production of vinyl chloride by thermal cracking of 1,2-dichloroethane in a cracking furnace, in which a medium pressure of from 1.4 to 2.5 MPa is maintained in the system and an externally heatable and separately regulatable heat exchanger is provided by means of which pressure fluctuations and temperature fluctuations within the system can be compensated for.

Other advantageous embodiments of the invention will be apparent from the subsidiary claims, the description and the FIGURE.

BRIEF DESCRIPTION OF THE FIGURE

FIG. 1 depicts a flow diagram of a process and a schematic illustration of the arrangement of an apparatus for the production of vinyl chloride. In FIG. 1A, the cracking furnace and the vaporization unit which makes primary use of the waste heat of the cracking gas stream are shown. In FIG. 1B, the quench column and the feed lines to the purification unit can be seen.

DETAILED DESCRIPTION OF THE INVENTION

According to one embodiment of the apparatus and of the process, the 1,2-dichloroethane is heated, before reaction thereof in the radiation zone of the cracking furnace, using the heat of the quench waste gas, that is to say, the waste heat of the top stream of the quench column. According to an especially preferred form of implementation, other waste heat of the system can also be used for heating the 1,2-dichloroethane that is to be introduced into the radiation zone of the cracking furnace. It is especially advantageous in that case for that system for heating the EDC to be additionally combined with a heat exchanger that leads through the convection zone of the cracking furnace and utilizes the waste heat of the flue gases of the cracking furnace.

The first heat exchanger may also be referred to as a trimming heat exchanger since, for example, in addition to regulating pressure, it can also be used as an externally vapour-operated heat exchanger for fine adjustment of the heat requirement in the EDC cracking.

That first heat exchanger, which can also be used for fine adjustment of the temperature of the 1,2-dichloroethane feedstock, is preferably arranged between a second heat exchanger, by which the waste gases of the top stream of the quench column are put to use, and a third heat exchanger that is integrated into the convection zone of the cracking furnace.

That external energy supply has proved advantageous for better regulation of the pressure in the cracking unit. In that manner, that is to say, by supplying external energy, the pressure fluctuations in the EDC vaporization and hence in the feed line can be compensated for. It is advantageous in that case for an automatic control system to be provided which measures the pressure in the EDC vaporization and, if the pressure changes, automatically or manually alters the temperature of the externally heated first heat exchanger in such a manner that the pressure returns to a predetermined value.

According to an especially preferred form of implementation, 1,2-dichloroethane is heated to almost boiling temperature in three stages, utilizing the energy content of the hot cracking gases and of the flue gases of the cracking furnace:

in the second heat exchanger, which utilizes the waste heat of the quench column, liquid 1,2-dichloroethane is heated to approximately 120-150° C. by the saturated vapour mixture (mainly comprising vinyl chloride, hydrogen chloride and unreacted 1,2-dichloroethane) that leaves the quench column at the top, in the first heat exchanger (trimming heat exchanger=vapour-operated heat exchanger for pressure regulation and/or fine adjustment of the heat requirement in the EDC cracking), the liquid 1,2-dichloroethane is further heated externally by steam, in a third heat exchanger in the convection zone of the cracking furnace, the 1,2-dichloroethane, which is still liquid, is heated by the flue gases of the cracking furnace to 200-250° C.

The 1,2-dichloroethane which is still liquid after that 3-stage heating process is vaporized in an external, so-called "EDC vaporizer" using the waste heat of the hot cracking gases having a temperature of 450-550° C. issuing from the cracking furnace, under a pressure of from 1.4 to 3.5 MPa, preferably from 1.4 to 2.5 MPa and especially from 1.6 to 2.2 MPa.

The then gaseous 1,2-dichloroethane is passed into the radiation zone of the cracking furnace and heated to above 450° C. within 5-10 seconds, preferably within 6-7 seconds. The energy supply to the cracking furnace is preferably distributed as follows:

| | |
|---|---|
| 1st burner row (EDC entry): | 30-70% |
| burner row(s) middle: | 20-40% |
| last burner row (cracking gas exit): | 10-20% |

The total residence time of the EDC in the radiation zone of the cracking furnace should be 15-30 seconds, preferably 18-23 seconds. The hot cracking gas having a temperature of from 450° C. to 550° C. is passed through the external EDC vaporizer and thereafter is cooled to saturated vapour temperature in the quench column by direct cooling with a liquid mixture of 1,2-dichloroethane, vinyl chloride and dissolved hydrogen chloride. The pressure in the quench column is 1.4-2 MPa, preferably 1.5-1.7 MPa.

The top stream of the quench is advantageously used for pre-heating liquid 1,2-dichloroethane and is then cooled to 50-60° C. with cooling water or by means of air coolers. The gas stream and the liquid stream from the quench system are then fed for distillation to separate hydrogen chloride, vinyl chloride and unreacted 1,2-dichloroethane. In the first stage, hydrogen chloride is separated from vinyl chloride and 1,2-dichloroethane over the top of the column. Owing to the quench pressure of 1.5-1.7 MPa, the first distillation column is operated at 1.2 MPa and −25° C. in the top.

In the upper portion of the convection zone of the cracking furnace, steam can be obtained and/or the combustion air for the cracking furnace can be pre-heated, while the flue gases are simultaneously cooled.

Surprisingly, it has been found that adherence to specific operating parameters, especially a pressure in the cracking coil of 1.6-1.9 MPa, to rapid heating of the 1,2-dichloroethane in the first portion of the radiation zone and adherence to the above-described residence times and/or specific firing in the individual cracking furnace segments drastically reduce the formation of by-products and at the same time prolong the operating time of the furnace. The refrigeration output required to liquefy the return material is, by virtue of the pressure in the first distillation column, only 35.4 kW/t of target product.

The EDC yield obtained (yield of vinyl chloride based on reacted pure 1,2-dichloroethane) according to the described process is 99.5%. Owing to the high entry temperature of the 1,2-dichloroethane into the radiation zone of the cracking furnace the consumption of primary energy in the cracking furnace is also very low in comparison with other, known processes.

The following Table shows the invention in comparison with the prior art DE 34 40 685 and EP 0 264 065 discussed in the introduction.

TABLE

Evaluation of the test results

| | according to the invention | similarly to EP 0 264 065 | similarly to DE 34 40 685 |
|---|---|---|---|
| formation of by-products in kg per tonne of target product | 11 | 17 | 10 |
| 1,2-dichloroethane yield in % by weight | 99.52 | 99.3 | 99.54 |
| total energy consumption of EDC cracking in kW/t of vinyl chloride | 904 | 890 | 943 |
| energy consumption of EDC vaporization in kW/t of vinyl chloride | 201 (by cracking gas) | 210 (by cracking gas) | 235 (by steam) |
| furnace operating time between cleaning periods in months | 19 | 10 | 20 |
| refrigeration output for liquefying the hydrogen chloride at the top of the HCl column in kW/t of target product | 35.4 | 33.7 | 92.5 |

DEFINITIONS formation of by-products=the sum of all the by-products resulting in the cracking of 1,2-dichloroethane 1,2-dichloroethane yield=yield of vinyl chloride based on the pure, reacted 1,2-dichloroethane total energy consumption: total primary energy used in the cracking furnace (tube reactor) in the form of heating gas or heating oil energy consumption of EDC vaporization: energy used to heat 1,2-dichloroethane in the EDC vaporizer to boiling temperature and for the total vaporization of the 1,2-dichloroethane stream to the cracking furnace (tube reactor); in the case of the high-pressure cracking and the invention that energy is extracted from the cracking gas after, it leaves the tube reactor, in the case of the low-pressure cracking that energy is supplied externally by means of steam.

furnace operating time=the time after which the reaction has to be discontinued in order to clean the cracking furnace (tube reactor).

refrigeration output for liquefying hydrogen chloride in the HCl column=the electrical energy that has to be used to generate cold in order to condense the quantity of hydrogen chloride required as return material in the first distillation column (HCl column).

The tabular presentation strikingly shows that the method according to the invention described herein makes it possible for the first time to obtain the three decisive advantages of low-pressure cracking, a high yield, a low rate of by-product formation and a long operating time of the furnace, with an energy consumption that bears comparison with high-pressure cracking.

The invention will also be described below with reference to a FIGURE that shows a flow diagram of a process and, the same time, a schematic illustration of the arrangement of an apparatus for the production of vinyl chloride.

The FIGURE is divided into two parts A and B. In the first part A, the cracking furnace and the vaporization unit which makes primary use of the waste heat of the cracking gas stream are shown. In the second part B, the quench column and the feed lines to the purification unit can be seen.

The process may be carried out, for example, as follows:

42 t/h of 1,2-dichloroethane at a temperature of 120° C. are brought to a pressure of 3.6 MPa by means of a pump 1 (sheet B) and pre-heated to approximately 160° C. via the second heat exchanger 7 (sheet B), which is heated by saturated vapour gas stream from the quench column, and via the first heat exchanger and the trimming heat exchanger 2 (sheet A) which is required to regulate the pressure in the EDC vaporizer, and are fed to the convection zone 3 (sheet A) of the cracking furnace 1 (sheet A). In the convection zone 3, the 1,2-dichloroethane is heated to 230° C. by means of the flue gases and, depending on the fill state of the external 1,2-dichloroethane vaporizer, is passed via a regulating valve into the EDC vaporizer 4 (sheet A). By means of the hot vinyl-chloride-containing cracking gases having a temperature of approximately 490° C. which flow through the tubes of the external 1,2-dichloroethane vaporizer, the 1,2-dichloroethane is heated to boiling temperature and vaporized at a pressure of 2.2 MPa. The hot 1,2-dichloroethane having a temperature of 232° C. is fed via a regulating valve to the upper portion of the radiation zone 5 of the cracking furnace 1 (sheet A). The cracking furnace 1 is fired, for example, with 1270 Nm³/h of natural gas. The distribution of the heating gas to the 4 rows of burners is, for example, as follows:

1st row top (EDC entry) approximately 40% of the total quantity of natural gas

2nd row top/middle approximately 30% of the total quantity of natural gas

3rd row bottom/middle approximately 18% of the total quantity of natural gas

4th row bottom (cracking gas exit) approximately 12% of the total quantity of natural gas The total conversion of 1,2-dichloroethane to vinyl chloride in the example actually carried out was 55.9%.

The cracking gas stream, consisting of vinyl chloride, 1,2-dichloroethane, hydrogen chloride and by-products, flows at approximately 490° C. out of the radiation zone of the cracking furnace into the external EDC vaporizer.

That stream is cooled to 260° C. in the vaporizer by vaporization of EDC and is fed to a quench column 6 (sheet B). The pressure in the top of the quench column 6 is 1.6 MPa. The cracking gas stream that has been saturated by means of a liquid mixture of 1,2-dichloroethane, vinyl chloride and hydrogen chloride is partially condensed in an air cooler 8 (sheet B). While regulating its level, the liquid is pumped from the recycling vessel 9 (sheet B) by means of a pump to a column in which HCl is separated over the top from VCM, unreacted EDC and by-products. The uncondensed gas stream is cooled in a further heat exchanger 10 (sheet B) and likewise fed to the above-mentioned distillation separation process.

The bottom stream from the quench column 6 is fed to a one-stage flash vessel 11 (sheet B) for separation of solids. The solids-free top stream of the flash vessel is condensed in a heat exchanger 12 (sheet B) and pumped to the above-mentioned distillation column. The vinyl-chloride-free and hydrogen-chloride-free bottom stream of the flash vessel is delivered for EDC purification by distillation.

For the entire system described herein by way of example a by-product balance was drawn up as follows:

analysis of feed 1,2-dichloroethane to the cracking furnace analysis of the hydrogen chloride stream of the HCl column to the oxychlorination analysis of the bottom stream of the HCl column to the vinyl chloride column analysis of the bottom stream of the flash vessel to the vacuum column The by-product balance corresponding to Example 1 gives 11 kg of by-products per tonne of target product (vinyl chloride) at a cracking conversion of 55.9%. The 1,2-dichloroethane yield was 99.52% (by weight).

The operating time of the cracking furnace until the next cleaning operation was 19 months.

The energy consumptions were as follows:
  energy consumption of the EDC cracking: 904 kW/t of vinyl chloride
  energy consumption for vaporization of 1,2-dichloroethane by means of cracking gas (already included in the 904 kW)
  electrical energy for liquefying hydrogen chloride at the top of the first distillation column: 35.4 kW/t of vinyl chloride According to further embodiments of the process, in addition to being used to heat the EDC, the convection zone of the cracking furnace serves to generate steam and/or to heat combustion air.

A further embodiment provides that the cooling of the cracking gases takes place for the most part within the quench by directly contacting the hot cracking gases with cooled, liquid EDC, vinyl chloride and hydrogen chloride which, for example, is sprayed into the quench in counter-current.

A further form of implementation provides that the cooling of the cracking gases takes place for the most part within the quench on column plates that are charged with cooled, liquid EDC from the top and in counter-current to the cracking gases.

A further form of implementation of the process is characterised in that the distribution of the heating medium of the cracking furnace to the individual rows of burners is regulated by measuring the product temperature per cracking furnace segment and regulating the fuel supply accordingly.

A further embodiment of the process is characterised in that the first distillation stage for removal of hydrogen chloride is operated under a condensation pressure of from 1.1 to 1.3 MPa and at a condensation temperature of from −22° C. to −26° C.

A further embodiment of the process is characterised in that the stream containing high-boilers and solids which issues from the bottom of the quench column is freed of solids in a one-stage vaporizer and is fed by pump to the column for removal of hydrogen chloride. The stream containing solids and high-boilers that has been freed of vinyl chloride and hydrogen chloride is fed for distillation to recover 1,2-dichloroethane.

A further form of implementation of the process is characterised in that the stream containing high-boilers and solids which issues from the bottom of the quench column is pre-purified in a sedimentation vessel to remove coarse solids particles and is then divided in a distillation column into a hydrogen-chloride-free and vinyl-chloride-free bottom stream, which consists for the most part of EDC, and a solids-free top stream, which contains the total proportion of hydrogen chloride and vinyl chloride. The distillate stream which has been freed of solids is fed, for example, by pump to the column for removal of hydrogen chloride. The bottom stream containing solids and high-boilers which has been freed of vinyl chloride and hydrogen chloride is then fed for distillation, for example to recover 1,2-dichloroethane.

A further form of implementation of the process is characterised in that the stream containing high-boilers and solids which issues from the bottom of the quench column is freed of solids in a two-stage vaporizer and is fed by pump to the column for separation of hydrogen chloride. The stream containing solids and high-boilers that has been freed of vinyl chloride and hydrogen chloride is then optionally fed for distillation to recover 1,2-dichloroethane.

A further form of implementation of the process is characterised in that, in the first distillation stage, a mixture of hydrogen chloride and vinyl chloride is removed over the top as distillate and a mixture of vinyl chloride and 1,2-dichloroethane is removed via the bottom of the column.

One form of implementation of the apparatus is characterised in that it comprises a trimming heat exchanger, an EDC cracking furnace comprising a convection zone and a radiation zone, a quench column having a heat exchanger at the top, an air and/or water cooler as a quench top condenser, at least one pump receiver, a quench bottom flash vessel, a quench bottom condenser and a heat exchanger for cooling the quench top gas stream before it enters the distillation.

By means of the invention disclosed herein it is possible for the first time to improve the energy balance of the thermal cracking of 1,2-dichloroethane, to reduce the residence time of the gases in the cracking furnace, to restrict the formation of by-products and thereby to prolong the operating time of the cracking furnace, that is to say the interval of time between two maintenance periods.

The invention relates to a process for the production of vinyl chloride by thermal cracking, in which the energy balance, the operating time of the cracking furnace and/or the yield of the reaction are distinctly enhanced in comparison with the prior art. A pressure of from 1.5 to 3.5 MPa is established in the cracking coil at a temperature of from 450 to 550° C. and, for pre-heating the EDC (=1,2-dichloroethane) introduced, inter alia the waste heat of the gas stream leaving the top of the quench column is utilized.

The invention claimed is:

1. A process for the production of vinyl chloride by thermal cracking of 1,2-dichloroethane in a cracking furnace, in which a medium pressure of from 1.4 to 2.5 MPa is maintained in the system and an externally heatable and separately regulatable first heat exchanger is provided by means of which pressure fluctuations and temperature fluctuations within the system can be compensated for, and wherein the EDC is introduced into the cracking furnace in gaseous form through an EDC feed line; and wherein a second heat exchanger is provided in the EDC feed line, wherein said second heat exchanger serves to heat the EDC that is to be introduced into the first heat exchanger.

2. A process according to claim 1, wherein a second heat exchanger brings the EDC to 120-150° C.

3. A process according to claim 1, wherein a third heat exchanger heats the EDC to 200-250° C.

4. A process according to claim 1, wherein the pressure in the cracking coil in the radiation zone of the cracking furnace is from 1.6 to 2.2 MPa.

5. A process according to claim 1, wherein the pressure in the cracking coil in the radiation zone of the cracking furnace is from 1.8 to 2.1 MPa.

6. A process according to claim 1, wherein the temperature in the cracking coil in the radiation zone of the cracking furnace is from 450 to 550° C.

7. A process according to claim 1, in which the EDC is heated in the cracking furnace to at least 450° C. within from 5 to 10 seconds.

8. A process according to claim 1, in which the total residence time of the EDC in the radiation zone of the cracking furnace is from 15 to 30 seconds.

9. A process according to claim 1, in which the energy supply to the cracking furnace is implemented in three burner row stages of which each stage may comprise one or more burners, the first burner row stage, at the EDC entry, providing from 30 to 70%, the second, middle burner row stage providing from 20 to 40% and the third burner row stage, at the exit of the cracking gases, providing from 10 to 20%.

10. A process according to claim 1, in which the pressure in the quench column is from 1.4 to 2 MPa.

* * * * *